United States Patent
Biedermann et al.

(10) Patent No.: US 6,918,911 B2
(45) Date of Patent: Jul. 19, 2005

(54) BONE ANCHORING DEVICE FOR STABILIZING BONE SEGMENTS AND SEAT PART OF A BONE ANCHORING DEVICE

(75) Inventors: Lutz Biedermann, Vs-Villingen (DE); Jürgen Harms, Karlsruhe (DE)

(73) Assignee: Biedermann Motech GmbH, VS-Schwenningen (DE)

(*) Notice: Subject to any disclaimer, the term of this patent is extended or adjusted under 35 U.S.C. 154(b) by 111 days.

(21) Appl. No.: 10/401,159

(22) Filed: Mar. 27, 2003

(65) Prior Publication Data

US 2003/0187439 A1 Oct. 2, 2003

(30) Foreign Application Priority Data

Mar. 27, 2002 (DE) .......................................... 102 13 855

(51) Int. Cl.$^7$ .............................................. A61B 17/56
(52) U.S. Cl. ............................................ 606/61; 606/73
(58) Field of Search ............................. 606/61, 73, 70, 606/71, 72, 60

(56) References Cited

U.S. PATENT DOCUMENTS

| | | | | |
|---|---|---|---|---|
| 5,443,467 A | * | 8/1995 | Biedermann et al. | 606/65 |
| 5,554,157 A | * | 9/1996 | Errico et al. | 606/61 |
| 5,690,630 A | * | 11/1997 | Errico et al. | 606/61 |
| 5,728,098 A | * | 3/1998 | Sherman et al. | 606/61 |
| 5,954,725 A | * | 9/1999 | Sherman et al. | 606/78 |
| 6,723,100 B2 | * | 4/2004 | Biedermann et al. | 606/73 |
| 2003/0004511 A1 | * | 1/2003 | Ferree | 606/61 |

FOREIGN PATENT DOCUMENTS

| | | |
|---|---|---|
| DE | 37 11 013 C1 | 6/1988 |
| DE | 39 23 996 C2 | 1/1991 |
| DE | 43 07 576 C1 | 4/1994 |
| FR | 2 624 720 * | 6/1989 |
| FR | 2 796 545 * | 1/2001 |

* cited by examiner

*Primary Examiner*—Pedro Philogene
(74) *Attorney, Agent, or Firm*—Barley Snyder LLC (57) ABSTRACT

The disclosure describes a receiver part for articulated connection of a bone anchoring element with a rod having a diameter. The bone anchoring element has a shank part and a head. The receiver part includes a first end and a second end opposite the first end. A bore extends from the first end in the direction of the second end for guiding through the shank part. Adjacent to the bore is a section for receiving the head. An opening extends from the second end in the direction of the first end for inserting the shank part with head. A recess extends from the second end in the direction of the first end for forming a channel with a bottom for receiving the rod, forming two open legs. Two slit-shaped recesses extending from the bottom of the channel in the direction of the first end.

20 Claims, 4 Drawing Sheets

BONE ANCHORING DEVICE FOR STABILIZING BONE SEGMENTS AND SEAT PART OF A BONE ANCHORING DEVICE

FIELD OF THE INVENTION

The invention relates to a bone anchoring device for stabilizing bone segments with a bone anchoring element and a seat part (receiver part) for articulated connection of the bone anchoring element to a rod and a receiver part of a bone anchoring device for stabilizing bone segments with a bone screw, a receiver part for articulated connection of the bone anchoring element to a rod, wherein the receiver part has a first and a second end, a bore extending from the first end in the direction of the second end for guiding through the screw shank, adjacent to the bore a section for receiving the screw head, an opening extending from the second end in the direction of the first end for inserting the shank with head, a recess extending from the second end in the direction of the first end for forming a channel for receiving the rod, forming two open legs, and two slit-shaped recesses extending at the front from the floor of the channel in the direction of the first end.

BACKGROUND OF THE INVENTION

From DE 37 11 013 C1 a pedicle screw for stabilizing spinal column segments is known, in which the screw element is articulatedly connected to a receiver part. The receiver part comprises two halves surrounding the head of the screw element and a guard ring holding them together. The receiver part further has receiving slits for inserting a threaded rod. Locking the head in the receiver part and fixing the threaded rod is done by nut-shaped fixing screws screwed on to the threaded rod on both sides of the receiver part, which fixing screws act laterally on the receiver part.

DE 39 23 996 C2 discloses a bone anchoring device for stabilizing bone segments with a bone screw, a receiver part for articulated connection of the bone anchoring element to a rod, wherein the receiver part has a first and a second end, a bore extending from the first end in the direction of the second end for guiding through the screw shank, adjacent to the bore a section for receiving the screw head, an opening extending from the second end in the direction of the first end for inserting the shank with head, a recess extending from the second end in the direction of the first end for forming a channel for receiving the rod, forming two open legs, and two slit-shaped recesses extending at the front from the floor of the channel in the direction of the first end. In the known device, to fix the angle of the bone screw relative to the receiver part, a pressure element acting on the head of the bone screw is provided. Fixing the rod, constructed as a threaded rod, takes place by means of nuts screwed on to the rod, which act laterally on the receiver part. In the assembled state a force is exerted on the head in the axial direction of the receiver part via the pressure element in such a way that the head is locked in the receiver part.

DE 43 07 576 C1 discloses a bone anchoring device in which there is a pressure element for fixing the head, wherein the bone anchoring device is for stabilizing bone segments with a bone screw, a-receiver part for articulated connection of the bone anchoring element to a rod, wherein the receiver part has a first and a second end, a bore extending from the first end in the direction of the second end for guiding through the screw shank, adjacent to the bore a section for receiving the screw head, an opening extending from the second end in the direction of the first end for inserting the shank with head, a recess extending from the second end in the direction of the first end for forming a channel for receiving the rod, forming two open legs, and two slit-shaped recesses extending at the front from the floor of the channel in the direction of the first end. Fixing the head and rod takes place by means of a fixing screw which can be screwed into the receiver part and a lock nut screwed on to the receiver part, which exert a force on the pressure element in the axial direction of the receiver part.

U.S. Pat. No. 5,728,098 also describes a bone anchoring device for stabilizing bone segments with a bone screw, a receiver part for articulated connection of the bone anchoring element to a rod, wherein the receiver part has a first and a second end, a bore extending from the first end in the direction of the second end for guiding through the screw shank, adjacent to the bore a section for receiving the screw head, an opening extending from the second end in the direction of the first end for inserting the shank with head, a recess extending from the second end in the direction of the first end for forming a channel for receiving the rod, forming two open legs, and two slit-shaped recesses extending at the front from the floor of the channel in the direction of the first end. Head and rod are fixed separately by two rings of memory shape alloy. For this purpose, the receiver part has a pair of opposite upper slots and a pair of opposite lower slots. Receiver part, screw and lower ring are pre-assembled loosely, and in this state, the bone anchoring device is screwed into the bone. Thereafter the rod is inserted and the upper ring is mounted. By the temperature of the body the two memory shape alloy rings contract. Thus, head and rod can be fixed separately in the receiver part by the two corresponding rings.

The object of the invention is to provide an improved bone anchoring device or a receiver part for same, wherein fewer components are required, which are easier for the user to handle and can be configured as more filigree from the point of view of dimensions.

SUMMARY OF THE INVENTION

The invention provides a receiver part for articulated connection of a bone anchoring element (1), which has a shank part (2) and a head (3), with a rod (12) with a first end (6) and a second end (7) opposite this, a bore (8) extending from the first end (6) in the direction of the second end (7) for guiding through the shank part (2), adjacent to the bore (8) a section (10; 60, 62) for receiving the head, an opening (9) extending from the second end (7) in the direction of the first end (6) for inserting the shank part with head, a recess (11) extending from the second end (7) in the direction of the first end (6) for forming a channel (11*b*) for inserting the rod, forming two open legs (13, 14), and two slit-shaped recesses (15) extending at the front from the floor of the channel (11*b*) in the direction of the first end (6), characterized in that the width of the channel (11*b*) with the rod (12) inserted is larger in the unloaded state than the diameter of the rod.

The invention also provides a bone anchoring device for stabilizing bone segments with a bone anchoring element (1) which has a shank part (2) and a head (3), a receiver part (5; 50) for articulated connection of the bone anchoring element (1) to a rod (12), wherein the receiver part (5; 50) has a first end (6) and a second end (7) opposite this, a bore (8) extending from the first end (6) in the direction of the second end (7) for guiding through the shank part (2), adjacent to the bore (8) a section (10; 60, 62) for receiving the head (3), an opening (9) extending from the second end (7) in the direction of the first end (6) for inserting the shank part with head, a recess (11) extending from the second end (7) in the direction of the first end for forming a channel (11b) for receiving the rod (12), forming two open legs (13, 14), and two slit-shaped recesses (15) extending at the front from the floor of the channel (11b) in the direction of the first end (6); characterized in that the width of the channel (11b) with the rod (12) inserted is larger in the unloaded state than the diameter of the rod.

Preferably, the invention also includes one or more of the following features:

- a device (16, 17; 16, 71, 72; 16, 71, 72, 78, 79) for exerting a force on the open legs to press the legs together;
- the section (10; 60, 62) for receiving the head (3) has a shape corresponding to the head to be received;
- the head (3) is constructed in the shape of a segment of a sphere and the section (10; 62) for receiving the head has a corresponding holder shaped like a segment of a sphere for the head;
- a separate insertion part (60) provided in the receiver part (5; 50) is provided for holding the head, wherein the insertion part has corresponding slit-shaped recesses (63) which come to overlap with slit-shaped recesses (15) in the inserted state;
- the device (16, 17; 16, 71, 72; 16, 71, 72, 78, 79) for exerting a force on the open legs comprises an outer thread (16) on the open legs and a nut (17; 71) with an inner thread cooperating with the outer thread;
- the measurements of the outer thread (16) and the nut (17) are chosen in such a way that the nut can be screwed down to such an extent that it presses on the inserted rod;
- the nut (71) is constructed in such a way that in the fully screwed down state it does not fix the rod and a rod fixing screw (76) is provided for fixing the rod;
- the outer thread (16) of the legs and the thread (72) of the nut (71) have in each case a section (78, 79) via which, when they cooperate, a pressure force is exerted on the open legs in a direction perpendicular to the slit-shaped recess; and
- the nut (71) is constructed in the form of a cap with a central bore (73) with a cylindrical projection (74) with inner thread (75) for receiving the rod fixing screw (76).

In the bone anchoring device according to the invention extremely secure clamping is produced by a combination of pressure forces acting laterally and in the axial direction of the receiver part.

BRIEF DESCRIPTION OF THE DRAWINGS

Further features and advantages of the invention emerge from the description of embodiment examples using the figures.

DETAILED DESCRIPTION OF THE INVENTION INCLUDING PREFERRED EMBODIMENTS

As can be seen from FIGS. 1 to 4, in a first embodiment the bone anchoring device has a screw element 1 with a thread section 2 with a bone thread and a head 3. The head 3 is constructed as shaped like a segment of a sphere adjacent to the thread section. Coaxially to the thread shaft and on the end opposite the thread section the head 3 has a recess 4 for bringing into engagement with a screwing tool.

The bone anchoring device further contains a receiver part 5, substantially constructed as cylindrical. The receiver part has a first end 6 and a second end 7 opposite it. Provided adjacent to the first end 6 is a bore 8 aligned as axially symmetrical, the diameter of which is larger than that of the thread section 2 and smaller than that of the head 3. The receiver part 5 further has a coaxial second bore 9, which is open on the end 7 of the receiver part opposite the first bore 8 and the diameter of which is large enough for the screw element 1 to be inserted through the open end with its thread section and its head. Between the first bore 8 and the second bore 9 is provided a coaxial section 10, which is immediately adjacent to the first bore 8 and is constructed in the shape of a segment of a sphere with a radius which is substantially identical to the radius of the section of the head 3 shaped like a segment of a sphere when the bone anchoring device is assembled and fixed. Because it is constructed in the shape of a segment of a sphere, the bore 9 is narrowed in such a way that section 10 forms a spherical holder for the head 3.

Figure 1:
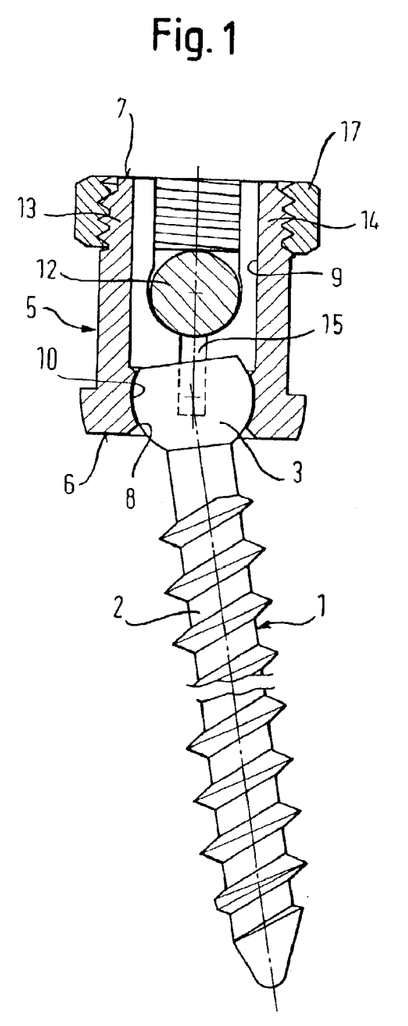
FIG. 1 shows a bone anchoring device according to a first embodiment in the assembled state illustrated in partial section.
Figure 2:
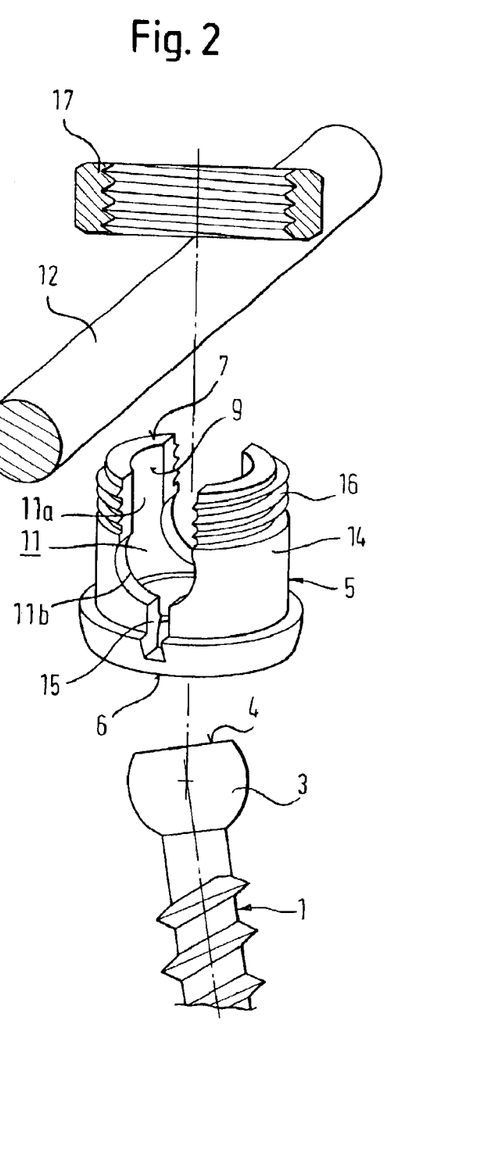
FIG. 2 shows the bone anchoring device of FIG. 1 in perspective exploded illustration.
Figure 3:
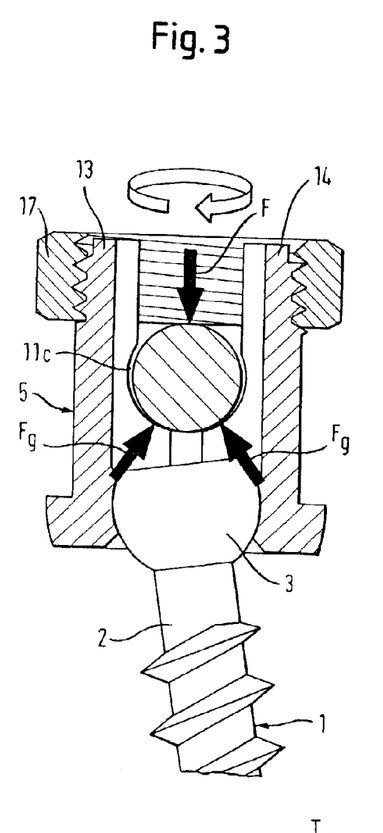
FIG. 3 shows the bone anchoring device of FIG. 1 illustrated in partial section in the unloaded state.

The receiver part 5 further has a recess 11, extending from the second end 7 in the direction of the first end, which is substantially U-shaped and forms a channel, into which a rod 12 can be inserted. Two open legs 13, 14 of the receiver part are formed by the recess 11. The recess 11 is further constructed in such a way that it has a first section 11a with a width which is dimensioned precisely so that the rod 12 can be inserted without jamming and a second area 11b, which forms the actual channel in which the rod 12 rests. Area 11b contains the floor of the channel and is constructed substantially as spherical with a widthways diameter which is larger than the diameter of the rod 12. Thus, as shown in FIG. 3, there is a small intermediate space 11c between the channel wall and the inserted rod, so the inserted rod 12 has a certain mobility crosswise to its longitudinal axis.

The receiver part 5 further has two slit-shaped recesses 15 opposite one another and extending at the front from the floor of the channel in the direction towards the first end 6. The recesses extend to a predetermined depth into section 10 shaped like a segment of a sphere. The width of the slit-shaped recesses 15 is dimensioned in such a way that the open 5 legs 13, 14 are elastically movable in respect of one another to a preset amount.

A section with an outer thread 16 is further constructed on the receiver part 5 in the area of the open legs 13, 14, adjacent to their open end 7. The outer thread 16 is constructed as a metric thread.

A nut 17 is provided, with an inner thread which cooperates with the outer thread 16. The length of the outer thread section and the measurements of the nut 17 in the axial direction are constructed in such a way that in the screwed in state the nut 17 presses on the rod 12.

In operation the screw element 1 is inserted from the open end of the second bore 9 into the first bore 8 until the head 3 with its lower side comes up against the upper edge of the section 10 shaped like a segment of a sphere and forming the spherical holder. On further insertion the legs 13, 14 are pressed apart slightly owing to their elasticity caused by the slit-shaped recess 15, so the screw head snaps into the spherical holder 10. There it is held as freely movable and the screw can be screwed into the bone by intervention of the screwing-in tool into the recess 4.

Figure 4:
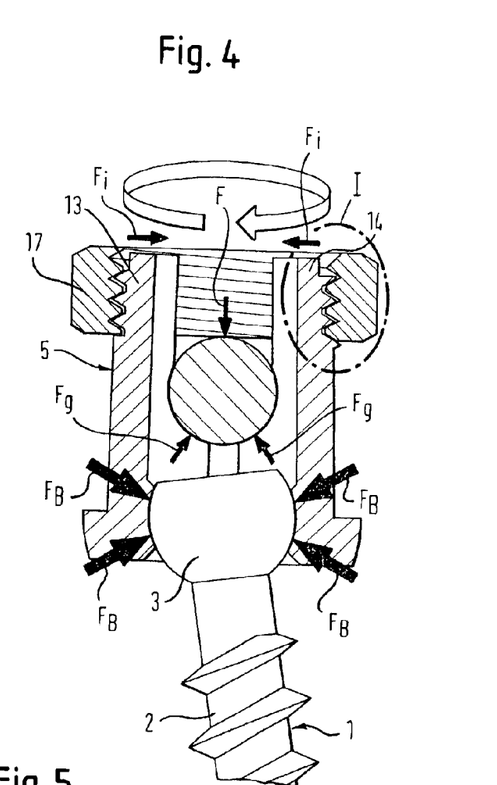
FIG. 4 shows the bone anchoring device of FIG. 1 in the loaded state.
Figure 5:
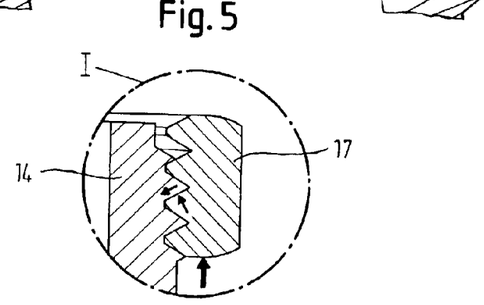
FIG. 5 shows the detail I of FIG. 4 in enlarged schematic illustration.

The rod 12 is then inserted and the nut 16 (sic) loosely screwed down. Accurate alignment of the receiver part 5 relative to the rod 12 then takes place. In this aligned position the nut 17 is tightened firmly in this way until it presses on the rod 12 with its end facing the rod and thus exerts a force, characterised by arrow F in FIG. 3, on the rod 12. The rod 12 is thus firmly clamped in the channel. The force F acting on the rod via the nut 17 generates counter-force components $F_G$ originating from the floor of the channel and illustrated by arrows $F_G$ in FIGS. 3 and 4. As illustrated in FIG. 5, this counter-force acts via the rod on the lower edge of the nut 17, whereby via the threaded flanks of nut and receiver part a force component Fi directed inwards (as illustrated in FIG. 4) is generated. Further screwing down of the nut 17 results in these counter-force components $F_G$ being of such a size that the legs 13, 14 undergo a force directed inwards of such a size that they are pressed together, this being possible owing to their elasticity caused by the slit-shaped recesses 15. The pressing together of the legs 13, 14 causes the spherical holder 10 to close firmly round the head shaped like a segment of a sphere and lock it in its position. This is illustrated in FIG. 4 by the radial force components $F_B$ acting on the spherical head and locking it. As can be seen in particular in FIGS. 3 and 4, the channel, spread out in the non-loaded state of the device, narrows in such a way that the rod 12 rests against the channel wall 11b.

Overall reliable fixing of rod and head is achieved with one single fixing element in the form of the nut 17.

Figure 6:
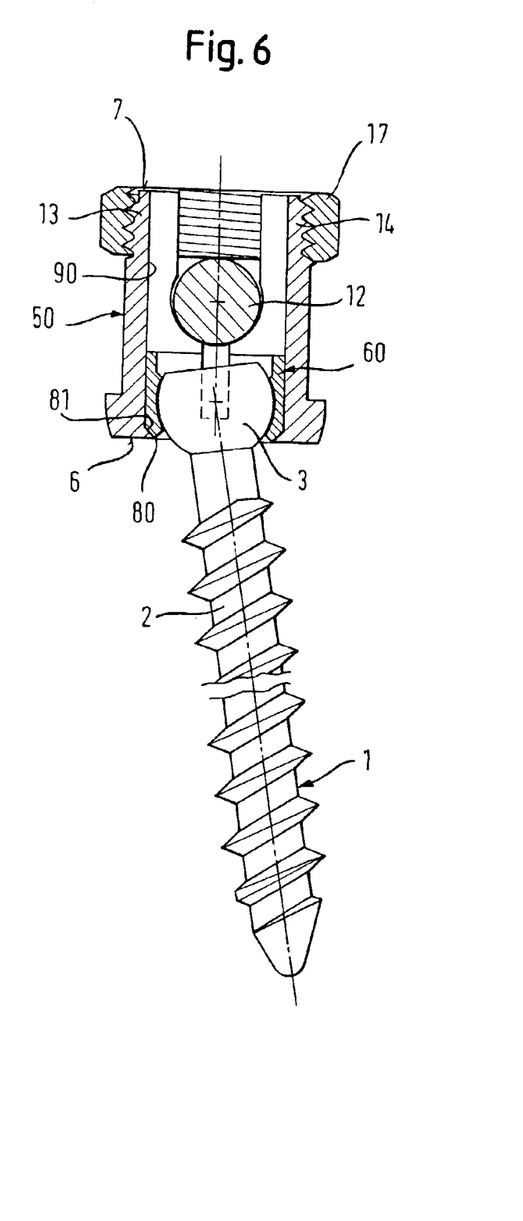
FIG. 6 shows a modified embodiment of the bone anchoring device of FIG. 1 illustrated in partial section.
Figure 7:
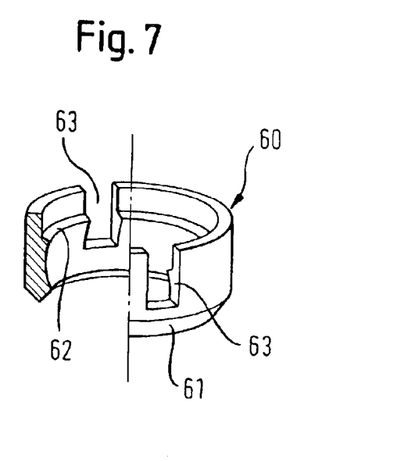
FIG. 7 shows an enlarged perspective sectionalised illustration of an element of the bone anchoring device according to FIG. 6.

In FIGS. 6 and 7 a modified embodiment of the bone anchoring device according to FIGS. 1 to 4 is shown which differs from the former in the holder of the head 3 in the receiver part 5. Identical parts are therefore described by the same reference numerals.

Receiver part 50 differs from receiver part 5 in that adjacent to the first end it has a first bore 80, the diameter of which is slightly larger than the diameter of the head 3 shaped like a segment of a sphere. The bore 80 widens over a small conical area 81 into a bore 90 extending as far as the second end 7.

Instead of the section 10 shaped like a segment of a sphere in the previously described embodiment, forming the holder for the head 3, in this embodiment the holder for the head 3 is formed by a separate insertion part 60.

The insertion part 60 is substantially constructed as hollow-cylindrical with a maximum outer diameter which is slightly smaller than the inner diameter of the bore 90, so part 60 can be inserted into the receiver part 90 starting from its second end 7. The insertion part 60 has a first end with a section 61, chamfered or tapering conically on the outer side, the angle of taper of which corresponds to the angle of taper of section 81 of the receiver part 50, so in the inserted state conical section 61 of insertion part 60 rests on conical section 81 of the receiver part.

On its inner side the insertion part 60 is constructed adjacent to conical area 61 with a section 62 shaped like a segment of a sphere similar to section 10 of receiver part 5 of the previously described embodiment, the radius of which substantially corresponds to the radius of the head 3. Section 62 shaped like a segment of a sphere forms the holder for the head 3.

The insertion part 60 further has on its end opposite conical section 61 two slit-shaped recesses 63, offset from one another by 180°, which extend to a predetermined length into section 62 shaped like a segment of a sphere. The width and depth of the recesses 63 are dimensioned in such a way that, when the insertion part 60 is inserted into the receiver part 50, the recesses 63 come to overlap with the slit-shaped recesses 15. The length of the insertion part 60 in the axial direction is less than the distance of the floor of the channel from the first end 6 of the receiver part 50.

Between the insertion part 60 and the inner wall of the receiver part there is further provided a safety device against twisting, not illustrated in the figures, so that the slit-shaped recesses 15 of the receiver part and the insertion part are not displaced in respect of one another while the screw element is being screwed into the bone. A safety device against twisting of this kind can be implemented, for example, by countersunk bores provided on the circumferential side of the insertion part 60, which cooperate with corresponding crimped bores on the receiver part.

In operation the screw element is first inserted into the insertion part 60 with its thread section 2 in the direction of conical section 61 until the head 3 snaps into the holder 62, made possible owing to the elasticity produced by the slit-shaped recesses. The insertion part 60 is then inserted into the receiver part 50 together with the screw element until conical section 61 of the insertion part rests on conical section 81 of the receiver part. The screw element is then screwed into the bone. Alignment of the receiver part and fixing the head 3 and rod 12 takes place via the nut 17, as in the first embodiment. The legs 13, 14 of the receiver part, moved towards one another, in this embodiment exert a clamping force on the head via the slit insertion part 60.

In a modification the slit-shaped recesses 63 of the insertion part are deeper than the recesses 15 of the receiver part 50. This makes insertion of the screw element easier owing to the greater elasticity of the insertion part, while the receiver part can be configured as sufficiently stable.

The embodiment containing the insertion part 60 has on the one hand the advantage that the receiver part 50 is easier to manufacture than in the first embodiment and on the other hand previous insertion of the screw element makes handling easier during application.

Figure 8:
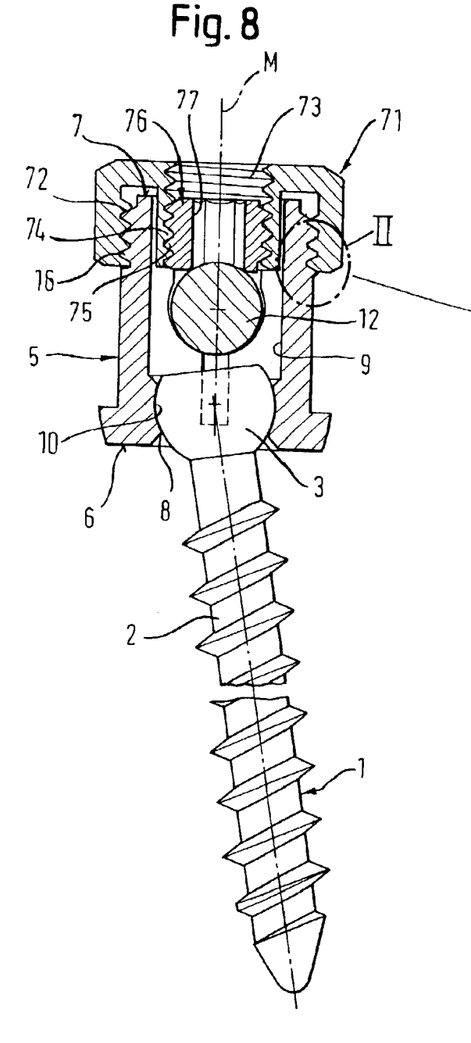
FIG. 8 shows a second embodiment of the bone anchoring device.
Figure 9:
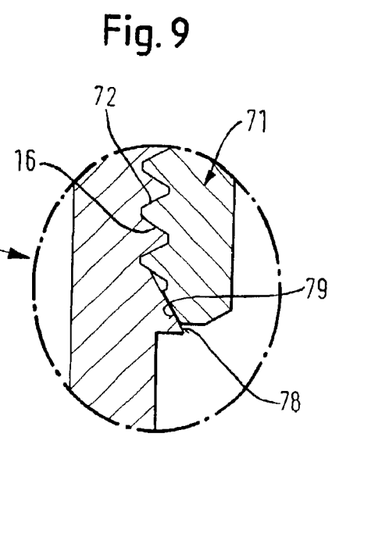
FIG. 9 shows an enlarged illustration of a detail II of a modification of the embodiment of FIG. 7.

The second embodiment illustrated in FIGS. 8 and 9 and its modification differs from the embodiment illustrated in FIGS. 1 to 7 in separate fixing of head 3 and rod 12.

In the embodiment illustrated in FIG. 8 the receiver part 5 is constructed like the receiver part according to FIGS. 1 to 5.

Instead of the nut 17 a cap 71 is provided, which has an inner thread 72 cooperating with the outer thread 16 of the receiver part 5. The cap 71 further has a central bore 73 and a cylindrical projection 74, extending therefrom in the direction of the open edge, with an inner thread 75 for receiving a rod fixing screw 76. The cylindrical projection 74 has a diameter which is slightly smaller than the inner diameter of bore 9 of the receiver part, so when the cap is screwed on the cylindrical projection slides into the receiver part and there is sufficient play towards the inner wall of the receiver part, so pressing together the legs to clamp the head is possible as in the first embodiment. The cylindrical projection 74 further forms a stop for the legs 13, 14 in such a way that the legs can be pressed together only far enough for the rod still to be freely displaceable in the channel. The rod fixing screw 76 is constructed as a set screw and has a recess 77 for bringing into engagement with a screwing-in tool. In the fully screwed down state of the cap (not illustrated in FIG. 8) the cap comes up against the open end 7 of the legs 13, 14, forming a stop. The measurements of the cap 71 and the length of the inner thread area of the cap are dimensioned in such a way that in the fully screwed down state the cap does not press on the inserted rod 12.

In operation the screw element is placed into the receiver part and screwed into the bone as in the first embodiment. The rod is then inserted and the cap 71 with screwed in rod fixing screw 76 is loosely screwed down. Adjustment of the position of the receiver part and adjustment of the rod are still possible in this state. Fully screwing down the cap as far as the stop, like screwing down the nut according to the first embodiment, causes the legs of the receiver part to be pressed together, leading to clamping of the head 3 in the holder, while the rod is still longitudinally displaceable in the channel. The rod is then fixed by further screwing in of the rod fixing screw 76 until its underside presses on the rod.

In FIG. 9 a modification of this embodiment is shown. The receiver part 5 is constructed as described previously, with the difference that on the end of the outer thread 16 facing the first end 6 of the receiver part in the outer wall of the receiver part a circulating diagonal face 78 is provided, which is aligned in the direction towards the first end 6 at an angle of approximately 30° to the central axis M of the receiver part.

Adjacent to the open edge of the cap 71, correspondingly provided on the inner side is a diagonal face 79 which cooperates with the diagonal face 78 of the receiver part in the screwed down state of the cap. The width of the diagonal face 79 of the cap is slightly smaller than the width of the diagonal face 78 of the receiver part, so when the cap is screwed down the faces can slide on one another to a certain extent.

In operation, in this modified embodiment when the cap is screwed down until it comes up against the open end of the legs the diagonal faces 78 and 79 end up on top of one another, wherein an additional force is exerted on the legs in the direction towards the central axis M of the receiver part, which presses the legs together.

In the embodiment illustrated in FIGS. 8 and 9 it is also possible to use the insertion part 60 according to the embodiment illustrated in FIGS. 6 and 7.

In the figures the slit-shaped recesses 15 of the receiver part 5 or 50 and the insertion part 60 are shown with a rectangular floor. However, they can also be constructed as rounded.

The invention has been described using an example of a bone screw. Instead of the bone screw hooks can be provided, wherein this is then constructed in two parts and has a head and a hook section which can be connected thereto, which is not connected until the head has been inserted.

The term rod is used above as representative of all rod-shaped elements and also includes these.

What is claimed is:

1. A receiver part for articulated connection of a bone anchoring element with a rod having a diameter, the bone anchoring element comprising a shank part and a head, the receiver part comprising:

a first end and a second end opposite the first end;

a bore extending from the first end in the direction of the second end for guiding through the shank part;

adjacent to the bore, a section for receiving the head, an opening extending from the second end in the direction of the first end for inserting the shank part with head;

a recess extending from the second end in the direction of the first end for forming a channel with a bottom for receiving the rod, the recess forming two open legs; and two slit-shaped recesses extending from the bottom of the channel in the direction of the first end, wherein the width of the channel with the rod inserted is larger in an unloaded state than the diameter of the rod; and wherein by pressing together the legs the head is locked in its position.

2. The receiver part in accord with claim 1, further comprising a device that cooperates with the two open legs to press the legs together.

3. The receiver part in accord with claim 1, wherein the section for receiving the head has a shape corresponding to the head to be received.

4. The receiver part in accord with claim 1, wherein the head has a shape of a segment of a sphere and the section for receiving the head has a corresponding shape to cooperate with the head.

5. The receiver part in accord with claim 1, further comprising a separate insertion part provided in the receiver part for holding the head, wherein the insertion part comprises corresponding slit-shaped recesses that overlap with said two slit-shaped recesses in the receiver part.

6. The receiver part in accord with claim 2, wherein the two open legs have an outer thread and the device that cooperates with the two open legs comprises a nut with an inner thread that cooperates with the outer thread on the two open legs.

7. The receiver part in accord with claim 6, wherein the outer thread and the nut each comprise the dimensions that are chosen in such a way that the nut can be screwed down to such an extent that it presses on an inserted rod.

8. The receiver part in accord with claim 6, wherein the nut is structured and arranged in such a way that, in the fully screwed down state, it does not fix an inserted rod and the receiver part further comprises a rod fixing screw for fixing the rod.

9. The receiver part in accord with claim 8, wherein the outer thread of the two open legs and the inner thread of the nut each comprise a cooperating portion whereby a pressure force can be exerted on the two open legs in a direction perpendicular to the slit-shaped recess.

10. The receiver part in accord with claim 8, wherein the nut is structured and arranged in the form of a cap having a central bore and a cylindrical projection surrounding the central bore and having an with inner thread for receiving the rod fixing screw.

11. A bone anchoring device for stabilizing bone segments, the device comprising:

a bone anchoring element comprising a shank part and a head;

a receiver part for articulated connection of the bone anchoring element to a rod;

the receiver part comprising:
- a first end and a second end opposite the first end;
- a bore extending from the first end in the direction of the second end for guiding through the shank part;
- adjacent to the bore, a section for receiving the head;
- an opening extending from the second end in the direction of the first end for inserting the shank part with head;
- a recess extending from the second end in the direction of the first end for forming a channel with a bottom for receiving the rod, the recess forming two open legs; and
- two slit-shaped recesses extending from the bottom of the channel in the direction of the first end, wherein the width of the channel with the rod inserted is larger in an unloaded state than the diameter of the rod.

12. The bone anchoring device in accord with claim 11, further comprising a device that cooperates with the two open legs to press the legs together.

13. The bone anchoring device in accord with claim 11, wherein the section for receiving the head has a shape corresponding to the head to be received.

14. The bone anchoring device in accord with claim 11, wherein the head has a shape of a segment of a sphere and the section for receiving the head has a corresponding shape to cooperate with the head.

15. The bone anchoring device in accord with claim 11, further comprising a separate insertion part provided in the receiver part for holding the head, wherein the insertion part comprises corresponding slit-shaped recesses that overlap with said two slit-shaped recesses in the receiver part.

16. The bone anchoring device in accord with claim 12, wherein the two open legs have an outer thread and the device that cooperates with the two open legs comprises a nut with an inner thread that cooperates with the outer thread on the two open legs.

17. The bone anchoring device in accord with claim 16, wherein the outer thread and the nut each comprise the dimensions that are chosen in such a way that the nut can be screwed down to such an extent that it presses on an inserted rod.

18. The bone anchoring device in accord with claim 16, wherein the nut is structured and arranged in such a way that, in the fully screwed down state, it does not fix an inserted rod and the receiver part further comprises a rod fixing screw for fixing the rod.

19. The bone anchoring device in accord with claim 18, wherein the outer thread of the two open legs and the inner thread of the nut each comprise a cooperating portion whereby a pressure force can be exerted on the two open legs in a direction perpendicular to the slit-shaped recess.

20. The receiver part in accord with claim 18, wherein the nut is structured and arranged in the form of a cap having a central bore and a cylindrical projection surrounding the central bore and having an with inner thread for receiving the rod fixing screw.

* * * * *

UNITED STATES PATENT AND TRADEMARK OFFICE
CERTIFICATE OF CORRECTION

PATENT NO. : 6,918,911 B2
DATED : July 19, 2005
INVENTOR(S) : Biedermann et al.

It is certified that error appears in the above-identified patent and that said Letters Patent is hereby corrected as shown below:

Title page,
Item [57], ABSTRACT,
Lines 9-10, "with head" should read -- with the head --.
Line 13, "extending" should read -- extend --.

Column 2,
Line 11, "U.S. Pat. No. 5,728,098" should read -- U.S. 5,728,098 --.

Column 4,
Line 3, "sectionalised" should read -- sectionalized --.

Column 5,
Line 16, "nut 16 (sic)" should read -- nut 17 --.

Column 8,
Line 43, "comprise the dimensions" should read -- comprise dimensions --.
Lines 45 and 48, "an inserted rod" should read -- the inserted rod --.
Line 60, "having an with inner thread" should read -- having an inner thread --.

Column 9,
Line 5, "with head" should read -- with the head --.

Column 10,
Lines 9-10, "comprise the dimensions" should read -- comprise dimensions --.
Lines 11 and 15, "an inserted rod" should read -- the inserted rod --.
Line 26, "having an with inner thread" should read -- having an inner thread --.

Signed and Sealed this

Sixth Day of December, 2005

JON W. DUDAS
*Director of the United States Patent and Trademark Office*